(12) United States Patent
Mohammad et al.

(10) Patent No.: US 10,894,929 B1
(45) Date of Patent: Jan. 19, 2021

(54) NATURAL GAS LIQUIDS RECOVERY PROCESS

(71) Applicant: Saudi Arabian Oil Company, Dhahran (SA)

(72) Inventors: Ayman M. Mohammad, Dammam (SA); Diki Andrian, Ras Tanura (SA); Yaqoub Y. Al-Kalaf, Dammam (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 16/590,806

(22) Filed: Oct. 2, 2019

(51) Int. Cl.
| | | |
|---|---|---|
| *C10L 3/10* | (2006.01) | |
| *C07C 7/00* | (2006.01) | |
| *C07C 7/11* | (2006.01) | |
| *C07C 7/04* | (2006.01) | |
| *B01D 53/04* | (2006.01) | |
| *F25J 3/02* | (2006.01) | |

(52) U.S. Cl.
CPC ............ *C10L 3/10* (2013.01); *B01D 53/0454* (2013.01); *C07C 7/005* (2013.01); *C07C 7/04* (2013.01); *C07C 7/11* (2013.01); *C10L 3/103* (2013.01); *C10L 3/104* (2013.01); *F25J 3/0209* (2013.01); *F25J 3/0238* (2013.01); *B01D 2256/24* (2013.01); *B01D 2257/7022* (2013.01); *C10L 2290/541* (2013.01); *C10L 2290/543* (2013.01); *C10L 2290/58* (2013.01); *C10L 2290/60* (2013.01); *F25J 2200/02* (2013.01); *F25J 2215/62* (2013.01)

(58) Field of Classification Search
CPC .. C10L 3/10; C10L 3/104; C10L 3/103; C10L 2290/58; C10L 2290/60; C10L 2290/54; C10L 2290/543; C07C 7/11; C07C 7/04; C07C 7/005; F25J 3/0238; F25J 3/0209; F25J 2215/62; F25J 2200/02; B01D 53/0454; B01D 2256/24; B01D 2257/7022
USPC ........ 585/802, 809, 833; 208/308, 311, 347, 208/351, 352
See application file for complete search history.

(56) References Cited

U.S. PATENT DOCUMENTS

| | | |
|---|---|---|
| 5,890,378 A | 4/1999 | Rambo et al. |
| 6,662,589 B1 | 12/2003 | Roberts et al. |
| 6,712,880 B2 | 3/2004 | Foglietta et al. |
| 6,742,358 B2 | 6/2004 | Wilkinson et al. |
| 7,159,417 B2 | 1/2007 | Foglietta et al. |
| 8,209,996 B2 | 7/2012 | Mak |
| 2008/0271480 A1 | 11/2008 | Mak |
| 2014/0060114 A1 | 3/2014 | Mak |

*Primary Examiner* — Thuan D Dang
(74) *Attorney, Agent, or Firm* — Fish & Richardson P.C.

(57) ABSTRACT

Methods and systems for operating and NGL recovery process are provided. In an exemplary method, an absorber column upstream of a fractionator column is operated at a higher pressure than a pressure in the fractionator column. An NGL ($C_3$ plus) stream is taken from the bottom of a fractionator column and then ethylene/ethane stream is taken from the top of the fractionator column. A differential pressure between the absorber column and the fraction are column is controlled based, at least in part, on a flow rate of the fractionator feed stream from the absorber column to the fractionator column.

17 Claims, 7 Drawing Sheets

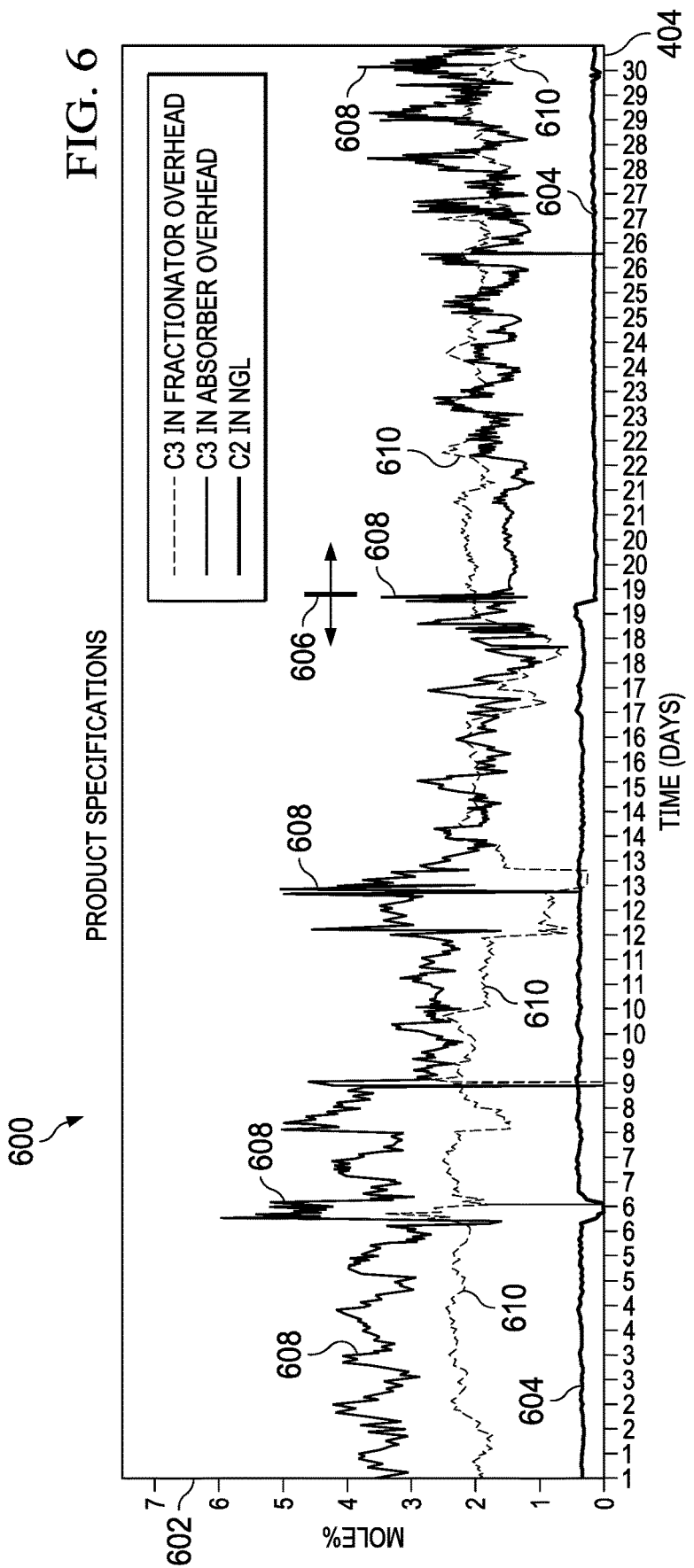

NATURAL GAS LIQUIDS RECOVERY PROCESS

TECHNICAL FIELD

The present disclosure relates to gas plants that are used for the production of natural gas liquids.

BACKGROUND

The processing of natural gas to prepare for pipeline sales or liquefaction involves a number of separations to isolate methane from other components or contaminants, such as crude oil, liquid water, water vapor, carbon dioxide, hydrogen sulfide, and other hydrocarbons. The separation of liquid water may be performed by a settling tank. The initial separation from crude oil, condensates, or both, if needed, may be performed by flashing or distillation. Other contaminants, including mercury and chlorides, among others, may be removed by techniques known in the art, such as wash columns.

Removal of acid gases, such as carbon dioxide, hydrogen sulfide, and others, is termed sweetening. Sweetening may be performed by passing the natural gas through an adsorption column, such as an amine absorber, to remove the acid gases from the natural gas. Newer technologies for sweetening have also been implemented, including gas membrane separators, among others.

Once the contaminants have been removed, methane, ethane, and ethylene may be separated from the other low boiling point hydrocarbons. These may include propane, butanes, and small amounts of higher molecular weight hydrocarbons, such as $C_5$ and $C_5$ plus. These materials are collectively termed natural gas liquids or NGL. The separation is generally performed by fractionation, often including low temperature distillation processes.

SUMMARY

An embodiment described in examples herein provides a method for operating a natural gas liquids (NGL) plant. The method includes operating an absorber column upstream of a fractionator column at a higher pressure than a pressure in the fractionator column. An NGL (C3+) stream is taken from a bottom of a fractionator column, and an ethane/ethylene stream is taken from a top of the fractionator column. A differential pressure between the absorber column and the fractionator column is controlled based, at least in part, on a flow rate of a fractionator feed stream from the absorber column to the fractionator column.

In an aspect, the pressure differential between the absorber column and the fractionator column can be controlled to keep the pressure in the absorber column to less than about 10% above the pressure in the fractionator column. Controlling the differential pressure may include adjusting the pressure on the fractionator column, while holding the pressure on the absorber column steady. Controlling the differential pressure may include adjusting the pressure on the absorber column while holding the pressure on the fractionator column steady.

In an aspect the method includes increasing the bottom temperature of the absorber column to increase flashing of C1 and C2. A reflux flow may be increased in the absorber column. A reflux flow may be increased in the fractionator column. A temperature of a feed gas to the absorber column may be increased to increase the stripping rate. A bottom temperature of the fractionator column may be decreased to decrease stripping of C3 plus compounds.

In an aspect the method includes increasing the differential pressure to increase the flow rate of the fractionator feed stream. The differential pressure may be decreased to decrease the flow rate of the fractionator feed stream.

In an aspect, the method includes measuring the flow rate of the fractionator feed stream, an overhead pressure in the absorber column, and an overhead pressure in the fractionator column. A new differential pressure is calculated based, at least in part, on a new set point for the flow rate of the fractionator feed stream. A first set point is calculated for an absorber column pressure controller and a second set point is calculated for a fractionator column pressure controller. The first set point is sent to the absorber column pressure controller and the second set point is sent to the fractionator column pressure controller.

In an aspect, the method includes setting an absorber column pressure controller to about 390 psig and setting a fractionator column pressure controller to about 350 psig.

In an aspect, the method includes deactivating a feed pump upstream of the fractionator column. The feed pump upstream of the fractionator column may be removed.

In an aspect, the method includes maintaining a fractionator column pressure controller at about 350 psig, and adjusting an absorber column pressure controller to adjust the flow rate of the fractionator feed stream to the fractionator column. A quench flow to the absorber column may be adjusted to enhance separation in a rectifying section.

Another embodiment described in examples herein provides a control system for operating columns in a natural gas liquids (NGL) plant. The control system includes a flow sensor to measure a flow rate of a fractionator column feed stream and an absorber column pressure controller. The absorber column pressure controller includes an absorber column pressure sensor and an absorber column pressure control valve. The control system also includes fractionator column pressure controller that includes a fractionator column pressure sensor, and a fractionator column pressure control valve. A controller is included in the control system. The controller includes a sensor interface to obtain measurements from the flow sensor, the absorber column pressure sensor, and the fractionator column pressure sensor. The controller also contains a controller interface to communicate set points to the absorber column pressure controller and the fractionator column pressure controller. A processor is included in the controller to execute stored instructions. A data store in the controller includes instructions configured to direct the processor to read measurements from the flow sensor, the absorber column pressure sensor, and the fractionator column pressure sensor and calculate a set point for the absorber column pressure controller based, at least in part, on a set point for the flow rate. Instructions are included in the data store to instruct the processor to adjust the set point for the absorber column pressure controller to match the calculated value.

In an aspect, the data store includes instructions configured to direct the processor to calculate a pressure differential between an absorber column and a fractionation column based, at least in part on the set point for the flow rate. Instructions are also included to calculate a new value for the set point for the absorber column pressure controller based, at least in part, on the pressure differential and adjust the set point based on the new value for the set point for the absorber column pressure controller.

In an aspect, the data store includes instructions configured to direct the processor to maintain the set point for the fractionator column pressure controller, while providing the new set point to the absorber column pressure controller.

In an aspect, the data store includes instructions configured to direct the processor to calculate a set point for the fractionator column pressure controller based, at least in part, on the set point for the flow rate, and adjust the set point for the fraction or column pressure controller to match the calculated set point for the fractionator column pressure controller.

In an aspect, the data store includes instructions configured to direct the processor to calculate a set point for the fractionator column pressure controller, based at least in part, on a set point for the flow rate and adjust the set point for the fractionator, pressure control of the match the calculated set point for the fractionator column pressure controller.

Another embodiment described in examples herein provides a natural gas liquids (NGL) plant. The NGL plant includes a chiller upstream of a gas-liquid separator, a gas line fluidically coupling a gas flow from the gas-liquid separator to an absorber column through a gas side of a heat exchanger, and a liquid line fluidically coupling the liquid flow from the gas-liquid separator to a fractionator column through a pump and the heat exchanger, where the liquid line couples to an opposite side of the heat exchanger from the gas line. A bottoms line from the absorber column fluidically couples to the liquid line to the fractionator column. A flow sensor on the liquid line, downstream of the heat exchanger, measures a flow rate of the fractionator column. An absorber column pressure sensor is located on an overhead line from the absorber column. An absorber column pressure control valve is located on the overhead line from the absorber column. A fractionator column pressure sensor is located on an overhead line from a fractionator reflux drum. A fractionator column pressure control valve is located on the overhead line from the fractionator accumulator.

In an aspect, the NGL plant includes a controller. The controller includes a sensor interface to obtain measurements from the flow sensor, the absorber column pressure sensor, and the fractionator column pressure sensor. The controller includes a controller interface to communicate set points to the absorber column pressure controller in the fractionator column pressure controller. The controller includes a processor configured to execute stored instructions and a data store including instructions configured to direct the processor to read measurements from the flow sensor, the absorber column pressure sensor, and the fractionator column pressure sensor. The data store includes instructions to direct the processor to calculate a set point for the absorber column pressure controller based, at least in part, on a set point for the flow rate, and adjust the set point for the absorber column pressure controller to match the calculated value for the set point for the absorber column pressure controller.

In an aspect, the NGL plant includes a liquid product pump coupled to a bottom of the fractionator column wherein the liquid product pump exports an LNG product.

BRIEF DESCRIPTION OF DRAWINGS

FIG. 6 is a plot of compositions of products for the NGL plant in mole percent versus time, showing the change in compositions during the process change.

DETAILED DESCRIPTION

Figure 1A:
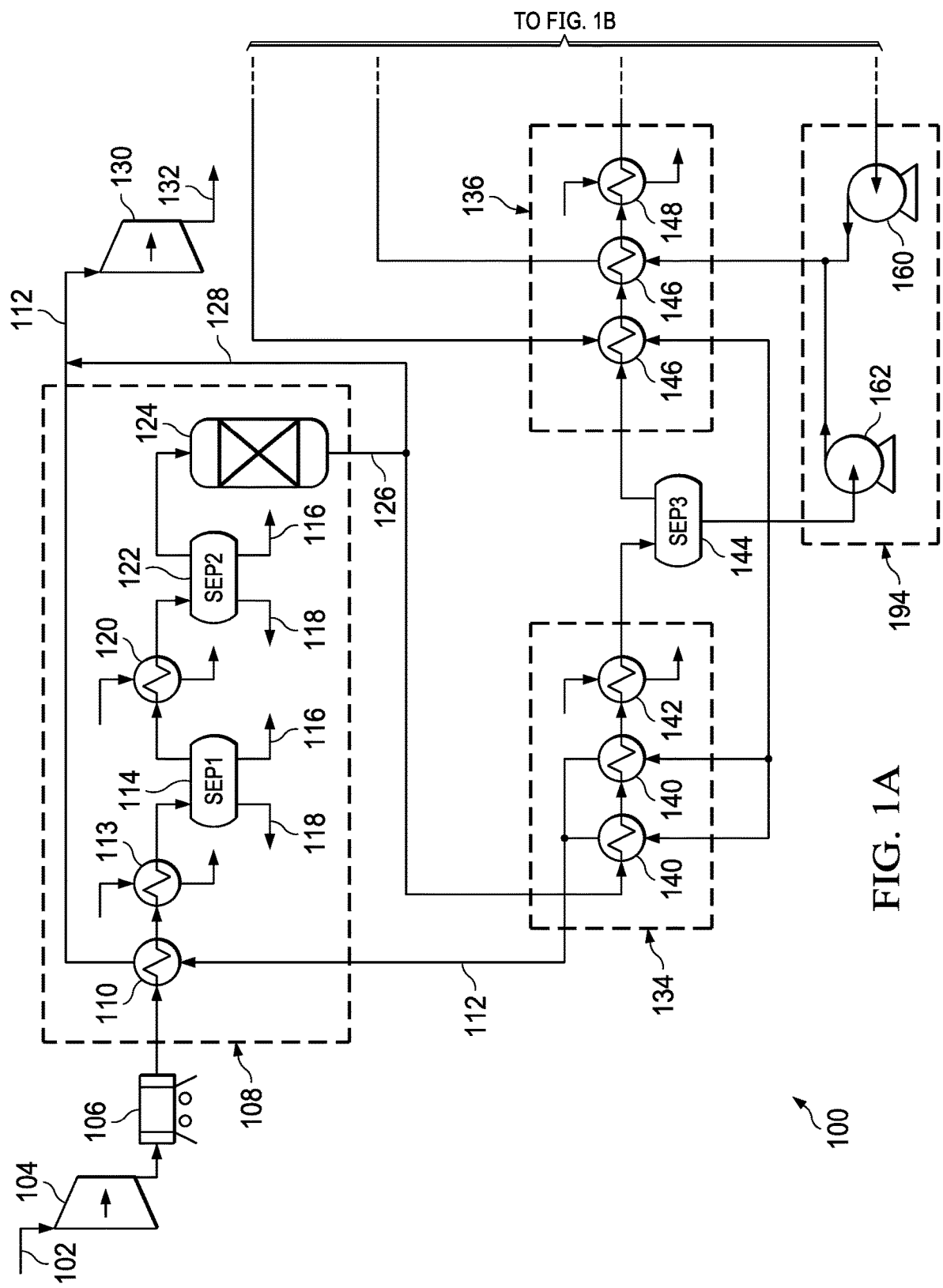
FIGS. 1A and 1B are a simplified process flow diagram of an NGL plant.

In a natural gas liquids (NGL) recovery process, propane and higher carbon compounds ($C_3$ plus) are extracted from a feed gas that also includes methane and ethane. To perform the process, the feed gas undergoes a series of cooling steps prior to being processed in an absorber column and fractionator column that performed the separation. The methane and ethane, generally in a single outlet stream, are then sent to a $C_2$ recovery plant, and the $C_3$ plus compounds are either sold or processed for further extraction, such as the isolation of $C_3$ compounds, $C_4$ compounds, $C_5$ compounds, and the like.

The feed gas may be sweetened by the removal of acid gases prior to cooling for the fractionation process. In some examples, the feed gas is compressed prior to beginning of process to a limit above column pressure and to accommodate the pressure drop across the plant, such as if the feed pressure is below about 440 kPa (about 50 psig), below about 790 kPa (about 100 psig), below about 1480 kPa (about 200 psig), or below about 2860 kPa (400 psig), or higher. The number of cooling stage varies, based on the target temperature for fractionating the feed gas, such as about −100° C. (about −148° F.), about −30° C. (about 5° F.) about −15° C. (about 5° F.), or about 0° C. (about 32° F.). Typically, the cooling is performed in three stages. Dehydrators are installed before the cryogenic process chilling stages, for example, after the first stage chilling is finished, to reduce water content to a low ppm level to avoid hydrate formation, such as about 50 ppm, about 25 ppm, about 10 ppm, about 5 ppm, about 1 ppm, or lower. In addition, a number of heat exchangers are installed to cool the feed gas as part of the heat integration between the colder streams farther downstream in the process and the harder streams farther upstream in the process.

After the feed gas is dehydrated and chilled to the target temperature, it is then fed into the absorber column. Typically, the absorber column is upstream of the fractionator column, and is intended to directly knock out unstable condensate and flash off light ends without having boil off liquid in the bottom. As used herein, "unstable condensate" refers to $C_3$ plus compounds, while "light ends" refers to $C_2$ and $C_1$ compounds, such as ethane, and methane.

Further separating of the light ends compounds from the bottom steam of $C_3$ plus is the purpose of the fractionator column. The fractionator has two reboilers at the bottom and a reflux system, including an accumulator, in the overhead. The accumulator is also termed a reflux drum, herein. A portion of the reflux stream from the accumulator is fed to the absorber to decrease the heavy end, such as $C_3$ plus compounds, from being carried over in the overhead stream. The unstable condensate from absorber, and from upstream separators, is fed to the fractionator column using reflux pumps. In the fractionator, the feed is further stabilized to produce on spec $C_3$ plus compounds from the bottom and flashing of the $C_1$ and $C_2$ compounds from the top. As used herein, "stabilized" refers to the removal of heavier compounds that may separate out in further operations on the $C_1$ and $C_2$ compounds. Generally, the fractionator is operated at a higher pressure than the absorber. Accordingly, a pump is used to deliver condensate from absorber column and other sources which are operated at lower pressure.

In examples described herein, the operating pressure of the absorber column is higher than fractionator column. This decreases or eliminates the need for pumps to provide feed to the fractionator column. At the tested boundary conditions, described in examples herein, the product specification is maintained or improved by adjusting other process variables in addition to the column pressure such as reflux rate, bottom temperature, and the differential pressure between two columns. The pressure of the product streams, including the overhead and bottom product streams, are sufficient to provide material to downstream process, such as at about 300 psig, 350 psig, 400 psig, or higher.

Figure 1B:
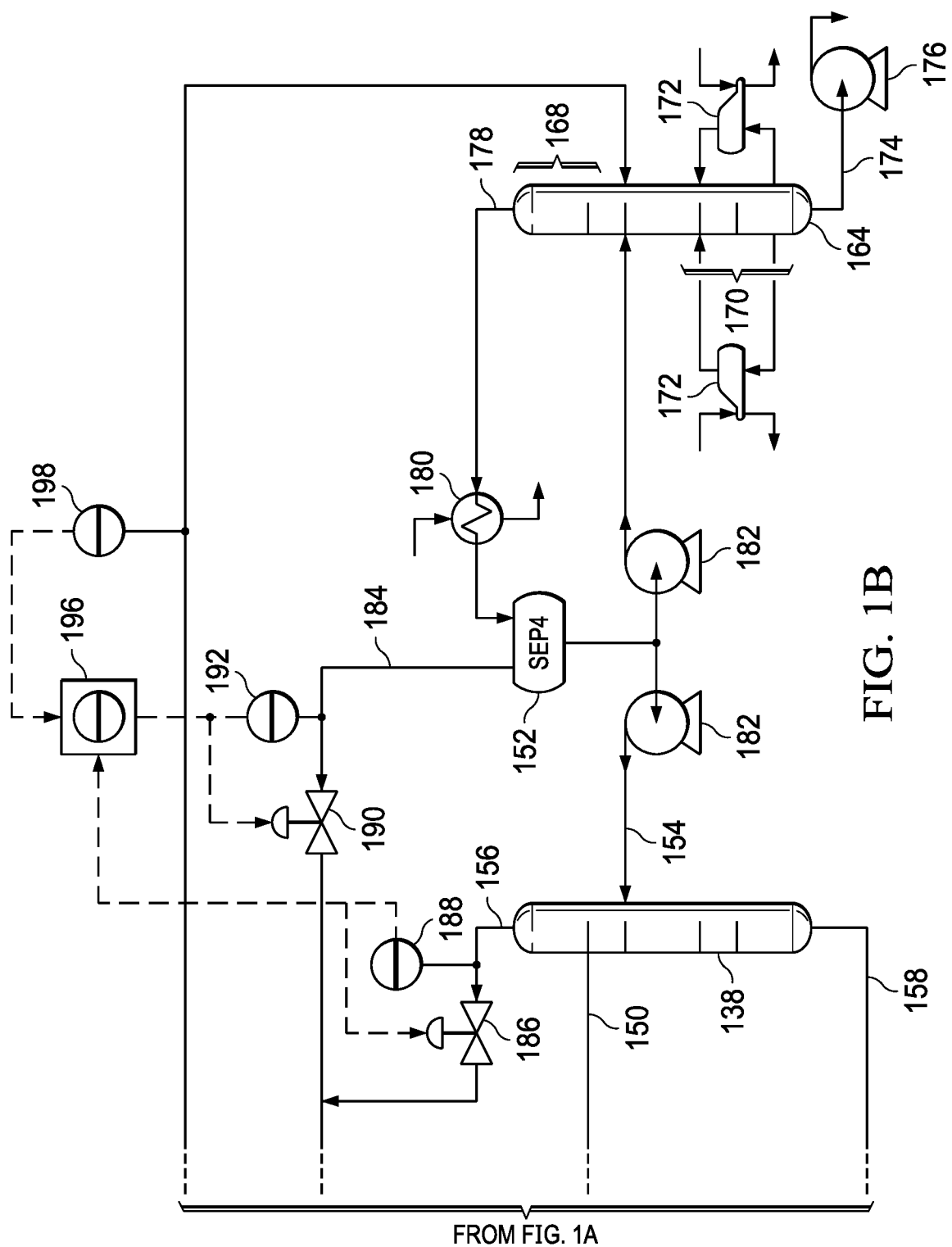

FIG. 1 is a simplified process flow diagram of an NGL plant 100. The NGL plant 100 receives a feed stream 102 that includes a saturated sweet gas. As used herein, "saturated" indicates that the gas is saturated with water vapor. As used herein, "sweet" indicates that the gas has been treated to remove acid gases, such as hydrogen sulfide and carbon dioxide.

The feed stream 102 is compressed by a feed gas compressor 104 suction scrubber. An aftercooler 106 cools the compressed feed gas to a temperature of less than about 50° C. (122° F.), less than about 60° C. (140° F.), or less than about 70° C. (158° F.), using ambient air as the heat exchange fluid. In an embodiment, the aftercooler 106 cools the compressed feed gas to a temperature of about 130° F. (about 54° C.).

The compressed feed gas then enters a first stage 108 of chilling. In the first stage 108 of chilling, the compressed feed gas is cooled down to less than about 20° C., less than about 25° C., or less than about 30° C., or higher in heat exchangers and a chiller which are operated in series. In the first heat exchanger 110, the compressed feed gas is cooled against the residue gas, carried in a residue gas line 112. The compressed feed gas is cooled in the first chiller 113 against propane refrigerant, before being sent to a three phase separator 114. In the three phase separator 114, hydrocarbon condensate and free water are separated from gaseous hydrocarbons. The hydrocarbon condensate is recycled to condensate stripper through a condensate line 116 and the free water is sent through a water line 118 for purification and disposal. The compressed feed gas is then fed to another chiller 120 for further cooling down prior to entering a second three phase separator 122 to remove further amounts of water and hydrocarbon.

From the second three phase separator 122, the compressed gas feed is fed to a dehydrator 124, in which molecular sieves, or other adsorbents, remove moisture from hydrocarbon vapors. After the dehydrator 124, the compressed gas feed includes less than about 10 ppm water, less than about 5 ppm water, less than about 1 ppm water, or lower. This helps to prevent hydrate formation at the lower processing temperatures further downstream. In an embodiment, compressed gas feed, termed dry gas, leaves the dehydrators at about 18° C. (65° F.) in a dry gas line 126.

Depending on the content of higher carbon number compounds, such as $C_2$ plus, in the dry gas, a bypass line 128 may be used to send the dry gas directly to a booster compressor 130. From the booster compressor 130, the dry gas may be sent to a $C_2$ recovery plant through a $C_2$ feed line 132. In some embodiments, the bypass line 128 is used if the dry gas includes less than about 1 vol. %, less than about 0.5 vol. %, less than about 0.1 vol. %, or lower. Further, the bypass line 128 may be used if the downstream separation equipment is being serviced.

To further chiller stages, a second stage 134 and a third stage 136 are used for cooling the dry gas to less than about −20° C., less than about −25° C., less than about −30° C., or less than about −35° C., before the dry gas is introduced to an absorber column 138. In an embodiment, the dry gas is cooled to about −32° C. (−25° F.) before it is introduced to the absorber column 138 as a cold feets gas.

The second stage 134 consists of two heat exchangers 140, where the source of cooling is from residue gas, and a chiller 142, where source of cooling is from propane refrigerant. The second stage 134 cools the feed gas to less than about −5° C., less than about −10° C., less than about −15° C., or less than about −20° C. In an embodiment, the dry gas is cooled to about −11° C. (about 12° F.), before it is introduced to a gas-liquid separator 144. Similarly, the third stage 136 includes two heat exchangers 146 and a chiller 148. The source of cooling for the heat exchangers 146 is from residue gas and unstable condensate from the absorber column 138. The source of cooling for the chiller 148 is from propane refrigerant.

The cold feed gas from the chiller 148 is introduced to the absorber column 138 through a gas feed line 150. Further, a liquid heavy end from a fractionator reflux drum 152 is fed to the absorber column 138 through a liquid line 154. An overhead line 156 from the absorber column 138 removes an absorber overhead stream that mainly includes methane and ethane.

The condensate carried by the bottoms line 158 from absorber column 138 is pumped by the absorber bottoms pump 160 and combined with the cold condensate coming from the gas-liquid separator 144 through a separator pump 162. The total condensate flow is preheated in second of the heat exchangers 146, before being fed to the fractionator column 164 for further stabilization through a fractionator feedline 166. As used herein, "stabilization" refers to the removal of higher carbon number compounds, such as $C_3$ plus, which may condense due to cooling from pressure decreases in downstream processes.

The fractionator column 164 has rectifying section 168 on the top and stripping section 170 on the bottom. In the stripping section 170, re-boiling takes place in two reboilers 172 which are heated by steam. The NGL product is removed from the column bottom through a NGL product line 174 and fed to downstream processes through one or more NGL shipping pumps 176. The overhead vapor from the fractionator column 164, exits through an overhead line 178, and is partially condensed in fractionator condenser 180. The fractionator condenser 180 is cooled by propane to a temperature of about −30° C., to about −40, or to about −50° C. In an embodiment, the temperature of the fractionator condenser 180 is set to about −39° C. (about −39° F.).

The fractionator condensate is collected in a collected in the fractionator reflux drum 152. Liquid condensate from the fractionator reflux drum 152 provides reflux to the absorber column 138 and the fractionator column 164 through reflux pumps 182. Off gas from fractionator reflux drum 152 contains mostly ethane and methane. The off gas exits the fractionator reflux drum 152 through an overhead line 184 and is combined with overhead vapors in the overhead line 156 from the absorber column 138 to form the plant residue gas stream in the residue gas line 112. As described herein, the plant residue gas stream in the residue gas line 112 is used to precool feed gas back to upstream through a series of heat exchanger, prior to being fed to the booster compressor 130.

The pressure in the absorber column 138 is controlled by an absorber column pressure control valve (PCV) 186 located on the overhead line 156 from the absorber column 138. The absorber column PCV 186 is controlled by an absorber column pressure controller 188 that includes an absorber column pressure sensor on the overhead line 156 to sense the pressure. The pressure in the fractionator column 164 is controlled by fractionator column pressure control valve (PCV) 190 located on the overhead line 184 from the fractionator reflux drum 152. The fractionator column PCV 190 is controlled by a fractionator column pressure controller 192 that includes a fractionator column pressure sensor on the overhead line 184 from the fractionator reflux drum 152.

Generally, the NGL plant 100 maintains the pressure of the absorber column 138 at about 2620 kPa (about 365 psig) and the fractionator column 164 at about 2860 kPa (about 400 psig). Accordingly, the absorber bottoms pump 160 and the separator pump 162, collectively referred to as the fractionator feed pumps 194, are used to provide feed from the lower pressure of the absorber column 138 to the higher pressure of the fractionator column 164. As a result, the delivery pressure for the gas product to a $C_2$ plant or the liquid LNG product to an LNG separation facility, remain in a favorable range.

In embodiments described herein, the column pressure in the absorber column 138 is set to be higher than the pressure in the fractionator column 164. This is described further with respect to FIG. 2. A controller 196 that is coupled to the pressure controllers 188 and 192 is used to control the pressures to maintain the feed flow from the absorber column 138 to the fractionator column 164, and, thus, the liquid outlet rate. Currently, the two pressure controllers 188 and 192 work independently, although both are automatically controlling. In various embodiments, the controller 196, or other calculator block, is used to keep the differential pressure to a level that is just sufficient to provide flow from the absorber column 138 to the fractionator column 164.

A flow sensor for the fractionating column feed stream, the fractionator column feed flow sensor 198, is located on the fractionator feedline 166 to provide the flow rate of the feed to the fractionator column 164 to the controller 196. The controller 196 is discussed further with respect to FIG. 3. Examples of the operation of the new set points are discussed with respect to FIGS. 4, 5, and 6. As described herein, this mode of operation may decrease the use of the fractionator feed pumps 194, and may allow their removal from the NGL plant 100.

Figure 2:
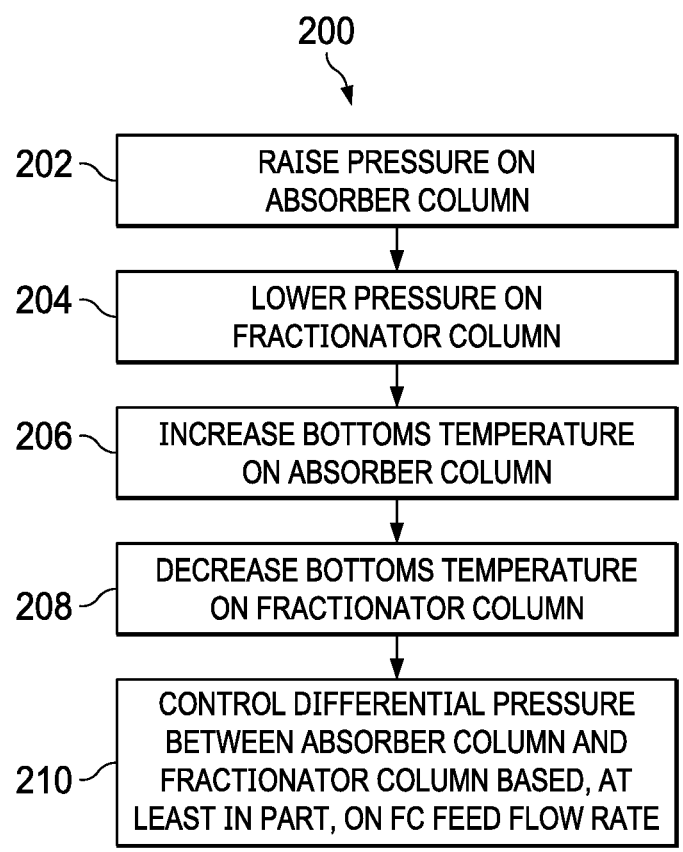
FIG. 2 is a flow chart of a method for operating the NGL plant.

FIG. 2 is a flow chart of a method 200 for operating the NGL plant 100. The method 200 begins at block 202 when the pressure is raised on the absorber column. The pressure may be set to about 2785 kPa (about 390 psig).

At block 204, the pressure is lowered on the fractionator column to about 2520 kPa (about 350 psig). The pressure differential between the absorber column and the fractionator column allows feed to flow from the absorber column, and the upstream separator, to the fractionator column without any required pumping. Accordingly, the fractionator feed pumps 194, described with respect to FIG. 1, may be eliminated. The reflux rate to the fractionator column is increased to compensate for a higher stripping rate in fractionator due to lower overhead pressure.

The new settings as optimum condition is about 2785 kPa (about 390 psig) for absorber and about 2520 kPa (about 350 psig) for fractionator to deliver flow from absorber and upstream separator to fractionator without any required pump. The differential pressure is adjustable based on liquid production. Moreover the feed gas compressor discharge pressure would be kept within the operation envelope while fractionator pressure at about 2520 kPa (about 350 psig) is adequate to dispatch the NGL product without a shipping pump, since the NGL header is much lower than this limit.

At block 206, the bottom temperature of the absorber column is increased by increasing the absorber feed temperature from −32° C. to −26° C. This to increase the flashing off of $C_1$ and $C_2$ compounds in the absorber columns. The rate of stripping of $C_3$ plus compounds is controlled by increasing reflux flow from overhead. In embodiments, the reflux, or quench, rate is increased to compensate for the increase in stripping. By doing so, the cooling required to precool the feed stream prior to entering absorber is reduced, and the temperature feed to absorber from second stage chiller is also increased to increase stripping rate. The overhead pressure tends to be increased by the increase in the stripping of the light end ($C_1$ and $C_2$). The increase of the reflux rate does increase the cooling duty on the reflux system, but lower than cooling duty on the feed absorber chillers.

At block 208, the bottom temperature of the fractionator column is decreased from 66° C. to 60° C. This decreases the rate of stripping of propane from the bottoms of the fractionator column while maintaining adequate stripping rate of $C_1$ and $C_2$ to maintain the NGL within desirable specifications. The amount of steam consumption used in the reboiler is decreased as a result. The reflux into the fractionator column is also increased to decrease the stripping.

At block 210, the differential pressure between the absorber column of the fractionator column is controlled based, at least in part, on the flow rate from the absorber to the fractionator column feed stream. The differential pressure is varying from 40 psig to 25 psig between the two columns based on the plant throughput. In some embodiments, the differential pressure may also be controlled, based at least in part, on the NGL outlet flow rate, for example, the loading on the plant. An advanced controller is used to set the pressure differential to be just sufficient to drive liquid from the absorber column to the fractionator column. If the plant loading is low, then the required differential pressure between the columns is also low. As it is not practical to operate the columns at floating pressure, the controller can anticipate disturbances from changing plant loading and composition.

The differential pressure may be adjusted based on liquid production. The overhead products from both columns can be merged despite having different overhead pressure by just simply operating the pressure control valves at the correct set point. With controlling differential pressure of both column as low as just sufficient top drive liquid delivered from absorber to fractionator, the combined pressure from column overhead remain high which favorable to the next processes. For instance, high suction pressure to booster compressor will help in reducing compression power.

From an energy perspective, the increase of the reflux to both columns implies an increase in the amount of cooling duty to the reflux condenser. However, this is offset by lower cooling duty on the feed absorber chiller and a decrease in steam consumption by the reboilers. Overall, energy consumption is reduced by powering down or removing the fractionator feed pumps that provide liquid from the absorber column to the fractionator column.

Figure 3:
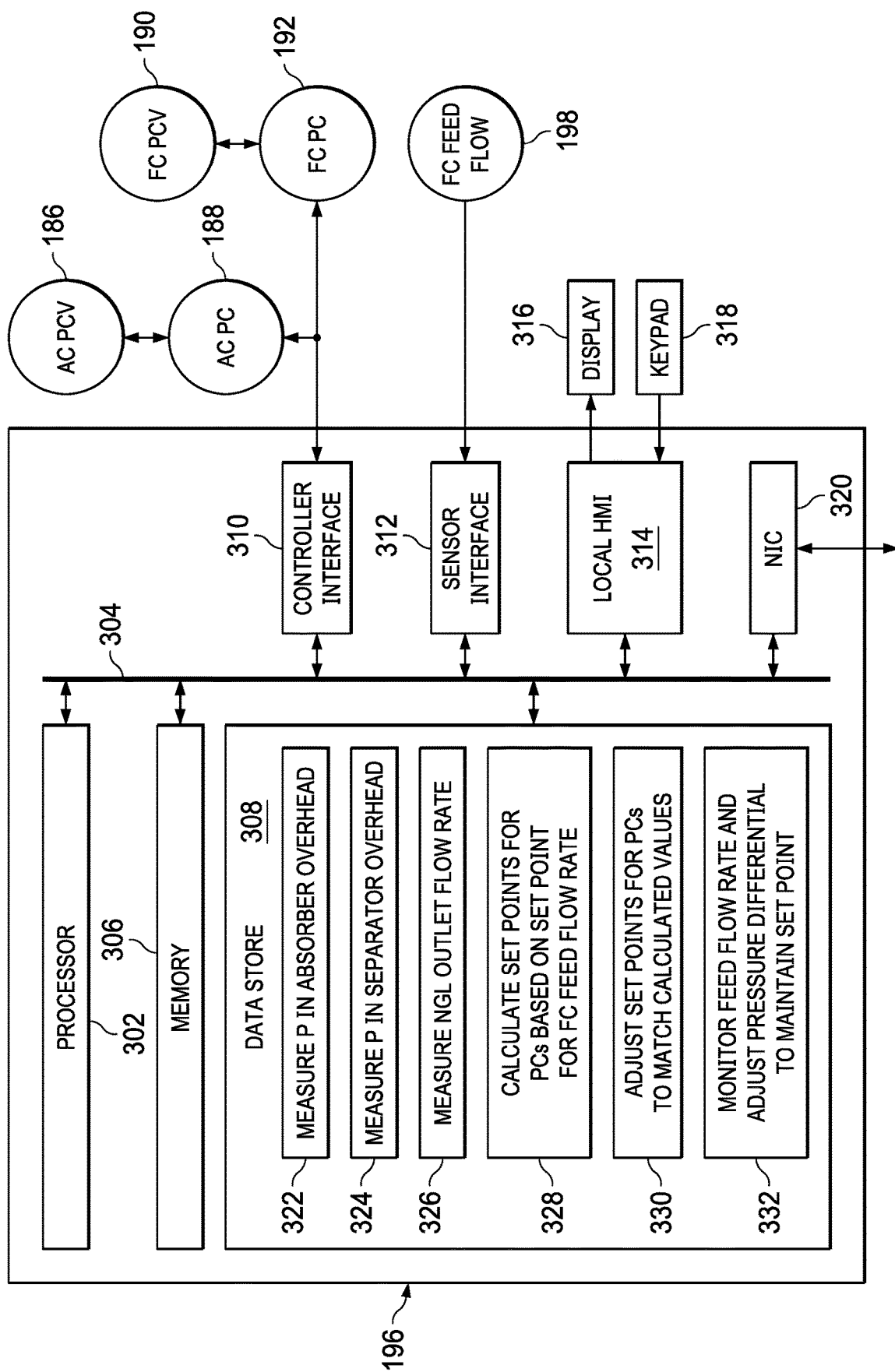
FIG. 3 is a block diagram of a controller for controlling the column pressures in the NGL plant.

FIG. 3 is a block diagram of a controller 196 for controlling the column pressures in the NGL plant 100. Like numbered items are as described with respect to FIG. 1. The controller 196 may be used to provide more robust process control and higher efficiency.

In some embodiments, the controller 196 may be a separate unit mounted in the field or plant, such as a programmable logic controller (PLC), for example, as part of a supervisory control and data acquisition (SCADA) or Fieldbus network. In other embodiments, the controller 196 may interface to a distributed control system (DCS) installed in a central control center. In still other embodiments, the controller 196 may be a virtual controller running on a processor in a DCS, on a virtual processor in a cloud server, or using other real or virtual processors.

The controller 196 includes a processor 302. The processor 302 may be a microprocessor, a multi-core processor, a multithreaded processor, an ultra-low-voltage processor, an embedded processor, or a virtual processor. The processor 302 may be part of a system-on-a-chip (SoC) in which the processor 302 and other components are formed into a single integrated package. In various embodiments, the processor may include processors from Intel® Corporation of Santa Clara, Calif., from Advanced Micro Devices, Inc. (AMD) of Sunnyvale, Calif., or from ARM holdings, LTD., of Cambridge England. Any number of other processors from other suppliers may also be used.

The processor 302 may communicate with other components of the controller 196 over a bus 304. The bus 304 may include any number of technologies, such as industry standard architecture (ISA), extended ISA (EISA), peripheral component interconnect (PCI), peripheral component interconnect extended (PCIx), PCI express (PCIe), or any number of other technologies. The bus 304 may be a proprietary bus, for example, used in an SoC based system. Other bus technologies may be used, in addition to, or instead of, the technologies above. For example, plant interface systems may include I2C buses, serial peripheral interface (SPI) buses, Fieldbus, and the like.

The bus 304 may couple the processor 302 to a memory 306. In some embodiments, such as in PLCs and other process control units, the memory 306 is integrated with a data store 308 used for long-term storage of programs and data. The memory 306 include any number of volatile and nonvolatile memory devices, such as volatile random-access memory (RAM), static random-access memory (SRAM), flash memory, and the like. In smaller devices, such as PLCs, the memory 306 may include registers associated with the processor itself. The data store 308 is used for the persistent storage of information, such as data, applications, operating systems, and so forth. The data store 308 may be a nonvolatile RAM, a solid-state disk drive, or a flash drive, among others. In some embodiments, the data store 308 will include a hard disk drive, such as a micro hard disk drive, a regular hard disk drive, or an array of hard disk drives, for example, associated with a DCS or a cloud server.

The bus 304 couples the controller 196 to a controller interface 310. The controller interface 310 may be an interface to a plant bus, such as a Fieldbus, an I2C bus, an SPI bus, and the like. The controller interface 310 couples the controller 196 to the absorber column pressure controller 188 for the absorber column and the fractionator column pressure controller 192 for the fractionating column. This allows the controller 196 to obtain values for the pressure measurements from the pressure controllers 188 and 192, and to communicate set points to the pressure controllers 188 and 192 for controlling the pressure control valves 186 and 190.

In some embodiments, sensors are used in place of the pressure controllers 188 and 192, and the pressure control valves 186 and 190 are directly controlled by the controller 196 or a plant control system, such as a DCS. In these embodiments, the pressure controllers 188 and 192 are virtual control blocks, or instructions, programmed in the DCS.

A sensor interface 312 couples the controller 196 to the fractionator column feed flow sensor 198 that measures the feed flown to the fractionating column. The sensor interface 312 may be integrated with the controller interface 310 as a single serial bus connection. Other sensors may be integrated with the system for determining parameters that may be used for the control algorithms, for example, a flow sensor on the NGL output from the bottoms of the fractionating column and a flow sensor on the residue gas.

If the controller 196 is located in the field, a local human machine interface (HMI) 314 may be used to input control parameters. The local HMI 314 may be coupled to a display 316, such as a multiline LCD display, or a display screen, among others. A keypad 318 may be coupled to the local HMI 314 for the entry of control parameters, such as the pressure differential between the absorber column pressure controller 188 and the fractionator column pressure controller 192.

In some embodiments, the controller 196 is linked to a plant control system, such as a DCS, through a network interface controller (NIC) 320. The NIC 320 can be an Ethernet interface, a wireless network interface, or a plant bus interface, such as Fieldbus. The controller 196 may be integrated with the controller interface 310, wherein the controller 196 is another note on the control bus coupled to the controller interface 310.

The data store 308 includes blocks of stored instructions that, when executed, direct the processor 302 to implement the functions of the controller 196. The data store 308 includes a block 322 of instructions to direct the processor to measure the pressure in the absorber overhead using the communications with the absorber column pressure controller 188. The data store 308 also includes a block 324 of instructions to direct the processor to measure the pressure in the fractionator reflux drum overhead from the fractionator column pressure controller 192. The pressure in the fractionator reflux drum corresponds to the pressure in the fractionator column. A block 326 of instructions directs the processor to measure the feed rate to the fractionating column using the fractionator column feed flow sensor 198 for the fractionator column feed.

The data store 308 includes a block 328 of instructions to direct the processor to calculate set points for the pressure controllers 188 and 192 based on the current pressure and flow measurements, and a set point for the feed flow rate. This may be calculated, for example, from the plant loading measured by flow sensors on the NGL and residue gas outlets. The data store includes a block 330 of instructions to direct the processor to adjust the set points for the pressure controllers 188 and 192 to match the calculated values, for example, through the controller interface 310.

A block 332 of instructions may be included in the data store 308 to direct the processor to monitor the feed flow rate and adjust the pressure differential between the absorber column pressure controller 188 and the fractionator column pressure controller 192 to maintain a feed flow as determined by the fractionator column feed flow sensor 198.

Any number of other blocks may be included in the data store 308 to implement other functions, including blocks of instructions to direct the processor to measure the NGL and residue gas flow rates. Complex control algorithms may also be included in blocks, such as block 332, in the data store 308.

In some embodiments, the complex control algorithms include models of the effects of the pressure changes in the absorber column and the fractionator column on feed flow to the fractionating column, NGL outlet flow, or residue gas flow, or any combinations thereof. The models may be statistical models and may include static or dynamic models, or include elements based on correlation between the columns differential pressure and flow from absorber to the fractionator. The models may be used to predict and adjust the set points for the absorber column pressure controller 188 and the fractionator column pressure controller 192 to maintain an appropriate differential pressure for the fractionating feed flow, the product flow, product pressure, and the like. To maintain smooth column operation, the pressure set point change is locked in one column and vary with second column with slow response step.

In an embodiment, a calculator block in the data store 308 includes instructions to direct the processor 302 to solve a linear equation of differential pressure as function of flow. Once the processor 302 obtains flow input from the fractionator column feed flow sensor 198, it will use the instructions of the calculator block to calculate the required differential pressure for delivering a desired flow of liquid from the absorber column to the fractionator column. The processor 302 will then use the instructions in block 332 with the resulting differential pressure to calculate the required differential pressure between the two columns. In some embodiments, one column, such as the absorber column, will be set at a fixed pressure and used as an input to block 332. Based on the calculated pressure differential, the output of block 332 is used as the set point for the pressure controller for a column, such as the fractionator column, which is operated at a floating pressure.

In some embodiments, the changes to the column pressures will be performed slowly to decrease the probability of process upsets that may result in decreases in product quality, for example, to maintain the product in an on-spec condition during the adjustments. As described herein, the process adjustments include the changes in flux flow, inlet temperature, and bottom temperature.

For example, if the feed to the absorber column is reduced, the required differential pressure is reduced to gain higher delivery pressure for the next processes, such as the booster compressor. If one column, such as the absorber column in this example, is set at a fixed pressure, the other column, such as the fractionator column in this example, will be operated at higher pressure based on the results of the calculator block. Thus, the pressure of the fractionator column will be increasing as the set point from block 332 is incrementally increased towards the new set point. Each increment increase in the pressure of the fractionator column will be performed along with an incremental increase in bottom temperature, to avoid a breakthrough of the light ends in the bottom product. Further, the reflux flow will be incrementally increased to lower the probability that heavier ends will escape from the column overhead. In addition, the reflux flow will also be increased due to the higher boiling rate caused by the higher bottom temperature.

Figure 4:
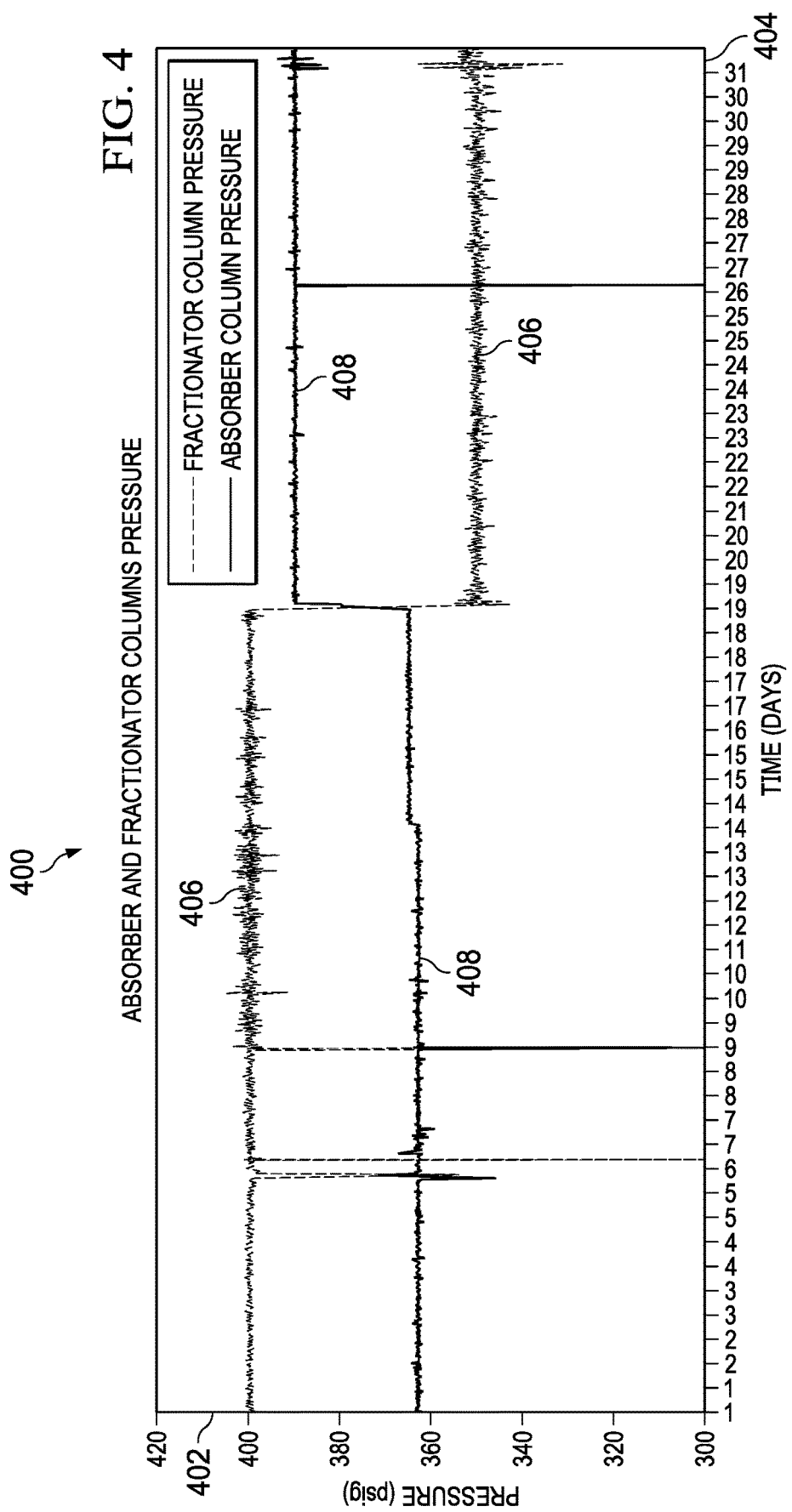
FIG. 4 is a plot of pressure versus time showing a change in the operating characteristics for the columns in the NGL plant.
Figure 5:
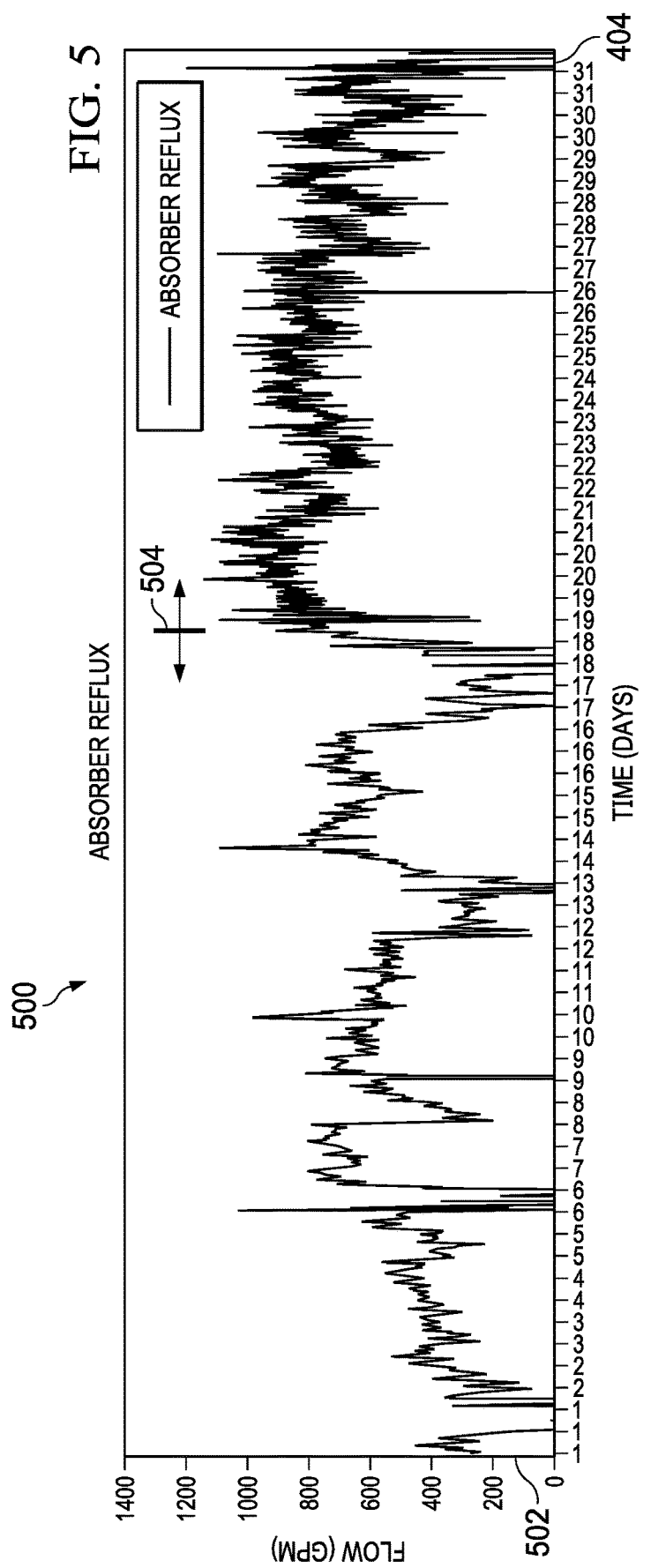
FIG. 5 is a plot of flow rate for reflux to an absorber column versus time showing the change in operating characteristics for the NGL plant.

The operating changes described herein were tested to determine the effects on operations and product purity as described with respect to FIGS. 4-6. The techniques were tested under various operating conditions, while measuring operating pressure, feed composition, flow rates, and temperature.

FIG. 4 is a plot 400 of pressure 402 versus time 404 showing a change in the operating characteristics for the columns in the NGL plant 100. The plot 400 covers a single month of operations in the NGL plant 100, during which the pressure changes took place on day 19. As shown in the plot 400, the fractionator column pressure 406 was initially set at about 400 psig (about 2860 kPa), while the absorber column pressure 408 was initially set to about 365 psig (about 2515 kPa). On day 19, the absorber column pressure 408 was increased to about 390 psig (about 2690 kPa) while the fractionator column pressure 406 was decreased to about 350 psig (about 2410 kPa). FIG. 5 discusses the changes made to the absorber reflux to control the process after the change in pressure, and FIG. 6 discusses the effects on the product specifications FIG. 5 is a plot 500 of flow rate 502 for reflux to the absorber column versus time 404 showing the change in operating characteristics for the NGL plant 100. The reflux flow rate was initially increased at the time 504 of the pressure change. This allowed more separation for C3+ compounds in the rectifying section and also to flash off methane and ethane from both the absorber column and the reflux drum. Further, this allowed operations to control the flow of the overhead stream from both columns.

FIG. 6 is a plot 600 of compositions of products for the NGL plant 100 in mole percent 602 versus time 404, showing the change in compositions during the process change. The ethane content 604 in the NGL product dropped from 0.5 mole % to 0.1 mole % when the pressure of the fractionator column was reduced 606 by 50 psig. This allowed more flashing of the ethane to the overhead stream.

A small improvement was seen in the propane in the overhead stream 608 from the absorber column as the increase in the reflux allowed better separation of the propane from the feed stream by quenching from the cold reflux. The propane in the overhead stream 610 from the fractionator column showed very little change.

Accordingly, the techniques described herein provide reliable and robust operations for a prolonged period. Further, with the powering down or removal of the fractionating feed pumps, the techniques are more efficient in terms of energy composition. Elimination of the pumps reduces operating expenses for plant installations and capital expenditures for new installations. The techniques are applicable for any typical NGL recovery processing plant. It revealed that the proposed line up is reliable to provide robust operations for a prolonged period and more efficient in term of energy consumption. Furthermore, this set up is applicable for any typical NGL recovery processes.

Other implementations are also within the scope of the following claims.

What is claimed is:

1. Method for operating a natural gas liquids (NGL) plant, comprising:
    operating an absorber column upstream of a fractionator column at a higher pressure than a pressure in the fractionator column;
    taking an NGL (C3+) stream from a bottom of the fractionator column and an ethane/ethylene stream from a top of the fractionator column; and
    controlling a differential pressure between the absorber column and the fractionator column based, at least in part, on a flow rate of a fractionator feed stream from the absorber column to the fractionator column.

2. The method of claim 1, comprising controlling the differential pressure between the absorber column and the fractionator column to keep the pressure in the absorber column to less than about 10% above the pressure in the fractionator column.

3. The method of claim 1, wherein controlling the differential pressure comprises adjusting the pressure on the fractionator column, while holding the pressure on the absorber column steady.

4. The method of claim 1, wherein controlling the differential pressure comprises adjusting the pressure on the absorber column, while holding the pressure on the fractionator column steady.

5. The method of claim 1, comprising increasing a bottom temperature of the absorber column to increase flashing of C1 and C2.

6. The method of claim 1, comprising increasing a reflux flow in the absorber column.

7. The method of claim 1, comprising increasing a reflux flow in the fractionator column.

8. The method of claim 1, comprising increasing a temperature of a feed gas to the absorber column to increase a stripping rate.

9. The method of claim 1, comprising decreasing a bottom temperature of the fractionator column to decrease stripping of C3 plus compounds.

10. The method of claim 1, comprising increasing the differential pressure to increase the flow rate of the fractionator feed stream.

11. The method of claim 1, comprising decreasing the differential pressure to decrease the flow rate of the fractionator feed stream.

12. The method of claim 1, comprising:
measuring the flow rate of the fractionator feed stream;
measuring an overhead pressure in the absorber column;
measuring an overhead pressure in the fractionator column;
calculating a new differential pressure based, at least in part, a new set point for the flow rate of the fractionator feed stream;
calculating a first set point for an absorber column pressure controller;
calculating a second set point for a fractionator column pressure controller;
sending the first set point to the absorber column pressure controller; and
sending the second set point to the fractionator column pressure controller.

13. The method of claim 1, comprising:
setting an absorber column pressure controller to about 390 psig; and
setting a fractionator column pressure controller to about 350 psig.

14. The method of claim 1, comprising deactivating a feed pump upstream of the fractionator column.

15. The method of claim 1, comprising removing a feed pump upstream of the fractionator column.

16. The method of claim 1, comprising:
maintaining a fractionator column pressure controller at about 350 psig; and
adjusting an absorber column pressure controller to adjust the flow rate of the fractionator feed stream to the fractionator column.

17. The method of claim 1, comprising adjusting a quench flow to the absorber column to enhance a separation in a rectifying section.

* * * * *